(12) United States Patent
Remde (10) Patent No.: US 8,870,830 B2
(45) Date of Patent: Oct. 28, 2014

(54) ADMINISTRATION DEVICE COMPRISING INDICATION UNIT AND METHOD FOR SETTING A DOSE

(75) Inventor: Axel Remde, Luetzelflueh (CH)

(73) Assignee: Roche Diagnostics International AG, Rotkreuz (CH)

( * ) Notice: Subject to any disclaimer, the term of this patent is extended or adjusted under 35 U.S.C. 154(b) by 681 days.

(21) Appl. No.: 12/778,634

(22) Filed: May 12, 2010

(65) Prior Publication Data

US 2011/0118700 A1 May 19, 2011

Related U.S. Application Data

(63) Continuation of application No. PCT/EP2008/009523, filed on Nov. 12, 2008.

(30) Foreign Application Priority Data

Nov. 13, 2007 (EP) .................... 07 021 986

(51) Int. Cl.
*A61M 5/00* (2006.01)
*A61M 5/315* (2006.01)
*A61M 5/31* (2006.01)

(52) U.S. Cl.
CPC ... *A61M 5/31525* (2013.01); *A61M 2005/3125* (2013.01); *A61M 2205/581* (2013.01); *A61M 2205/50* (2013.01); *A61M 2205/52* (2013.01); *A61M 2205/587* (2013.01); *A61M 2205/3584* (2013.01); *A61M 2205/582* (2013.01); *A61M 2005/3126* (2013.01); *A61M 2205/583* (2013.01)
USPC .............. 604/207; 604/66; 604/503; 604/506

(58) Field of Classification Search
USPC ................... 604/66, 131, 151, 181, 183, 186, 604/207–211, 890.1, 500, 503, 504, 604/506–508, 511, 512
See application file for complete search history.

(56) References Cited

U.S. PATENT DOCUMENTS 6,482,185 B1   11/2002  Hartmann
7,931,613 B2 *  4/2011  Haueter et al. .................. 604/66

FOREIGN PATENT DOCUMENTS

| DE | 29904864 | 8/2000 |
|---|---|---|
| EP | 1498067 A1 | 1/2005 |
| WO | 93/16740 A2 | 9/1993 |
| WO | 97/36625 A1 | 10/1997 |
| WO | 2007/056592 A2 | 5/2007 |
| WO | 2007/107431 A1 | 9/2007 |

* cited by examiner

*Primary Examiner* — Kami A Bosworth
(74) *Attorney, Agent, or Firm* — Dinsmore & Shohl LLP (57) ABSTRACT

An administration device for the administration of a liquid drug in adjustable doses may comprise an injection unit and an electronic indication unit. The injection unit may comprise a dosing mechanism and a manually operated dose setting component. The manually operated dose setting component may adjust the dosing mechanism to administer an administration dose amount of the liquid drug. The electronic indication unit may indicate a relationship between the administration dose amount and a target dose amount. A method for setting a dose of a liquid drug for administration may comprise providing an administration device, operating a manually operated dose setting component of the administration device, and continuing to operate the dose setting component until an electronic indication unit indicates that the administration dose amount is equal to the target dose amount.

21 Claims, 4 Drawing Sheets

FIG. 4

ADMINISTRATION DEVICE COMPRISING INDICATION UNIT AND METHOD FOR SETTING A DOSE

CROSS-REFERENCE TO RELATED APPLICATIONS

The present application is filed under 35 U.S.C. §111(a) as a continuation of International Application No. PCT/EP2008/009523, with an international filing date of Nov. 12, 2008. The present application claims priority under 35 U.S.C. §119 to European Patent Application No. 07 021 986.0, filed Nov. 13, 2007.

TECHNICAL FIELD

The present disclosure is related to devices for administering drugs, and more particularly to administration devices for administering a liquid drug in adjustable doses and to methods for setting a dose of a liquid drug.

BACKGROUND

In the therapy of insulin-dependent diabetes mellitus, pen-shaped administration devices for the self-administration of insulin in adjustable doses are widely used and well known in the art. Such devices may be designed for ejecting a single, pre-installed insulin reservoir and to be disposed after fully emptying the reservoir. Such a device is disclosed in WO 97/36625. Other devices are designed for multiple use with the insulin reservoir being exchanged after emptying. Such devices may be of a more complicated design and may be equipped with an electronics module, e.g., for dose displaying purposes, such as the device disclosed in WO 93/16740. Often several of such administration devices are being used by one patient with, e.g., one administration device generally kept at home and another administration device at the workplace. Furthermore, therapy is often performed with more than one type of insulin, the different types of insulin being administered at different times of day and with different doses. Each of the insulin types is administered with a different administration device. Besides the therapy of insulin-dependent diabetes mellitus, similar devices are used for the administration of other liquid drugs, such as pain relievers or growth hormones.

In U.S. Pat. No. 6,482,185 an administration device is disclosed, the administration device comprising an injection pen adapted for the self-administration of insulin in adjustable doses and an external display apparatus for enlarged displaying the injection dose. The display apparatus may further comprise one or more component for entering carbohydrate data and a dose calculator for calculating an insulin dose to be injected. The external display device is bulky and has to be separated from the pen before insulin administration. This results in a number of drawbacks, partly related to user comfort which is known to directly influence acceptance.

Administration devices having one or more manually operated dose entry component, as do typical insulin pens, often are prone to user error during the manual setting of the dose. Such errors may result in unintended over-administration or under-administration of the drug. According to the disclosure of U.S. Pat. No. 6,482,185, this problem may be resolved by integrating a drive into the external display apparatus, the drive being operationally coupled to the dose calculator and the injection pen, such that a dose amount calculated by the dose calculator is automatically set. This approach, however, results in a rather complex, bulky and expensive electromechanical system. There remains an ongoing need for improved liquid and drug administration devices not prone to dosing errors.

SUMMARY

An administration device for administering a liquid drug in adjustable doses may comprise an injection unit with manually operated dose setting components and a dosing mechanism. The manually operated dose setting components may be configured to adjust the dosing mechanism to administer an administration dose amount AD of the liquid drug. The administration device may further comprise an electronic indication unit that indicates a relationship, for example, the arithmetic difference, between the administration dose amount AD and a target dose amount TD.

In some embodiments, the indication unit may further comprise at least one of an acoustic indicator, such as a buzzer, and a tactile indicator, such as a vibrator. An acoustic indicator or a tactile indicator may be activated, for example, if the administration dose amount AD equals the target dose amount TD or if administration dose amount AD does not equal the target dose amount TD.

In still further example embodiments, the administration device may further comprise a data interface. The data interface may serve several purposes, such as the transmission of configuration data from an external device to the administration device. The administration device may store the delivered amounts of administered doses in a history memory together with a time stamp. In specific example embodiments, the data interface is a bidirectional interface and may be a wireless infrared interface or an RF interface such as a BLUETOOTH interface. The external device may be, for example, a Personal Computer (PC), a mobile phone, a Personal Digital Assistant (PDA), or an application specific device.

In some embodiments, all components of the administration device may be enclosed within an elongated housing, such as a pen-shaped housing. Alternatively, the components of the administration device may be enclosed by a plurality of housings adapted to be physically connected so as to have an overall elongated shape, such as a pen-like shape.

In alternative embodiments, the administration device may be configured as a dual-module administration device comprising an injection module and a supplementary module. In this type of embodiment, the injection module comprises the injection unit and the indication unit. The injection module further comprises an injection module data interface and an injection module housing. The supplementary module comprises a supplementary module data interface and a supplementary module housing.

In further alternative embodiments, the administration device also comprises an injection module and a supplementary module. The injection module comprises the injection unit and further comprises an injection module data interface and an injection module housing. The supplementary module comprises the indication unit and further comprises a supplementary module data interface and a supplementary module housing.

Further example embodiments described herein relate to methods for setting a dose amount of a liquid drug for administration. In one example embodiment, a method for setting a dose amount may comprise providing an administration device according to one or more embodiments described herein. For example, the administration device may comprise an injection unit and an indication unit. The injection unit may have a dosing mechanism and a manually operated dose setting component configured to adjust the dosing mechanism to administer an administration dose amount of the liquid drug. The indication unit may be configured to indicate a relationship between the administration dose amount and a target dose amount stored in or entered into the administration device. The method may further comprise operating the manually operated dose setting component to adjust the dosing mechanism to correspond to an administration dose amount relative to the target dose amount. The method may further comprise continuing to operate the manually operated dose setting component until the indication unit indicates that the administration dose amount is equal to the target dose amount.

In specific example embodiments, the methods for setting a dose amount of a liquid drug may be applied for the administration of insulin in the framework of diabetes mellitus therapy. Even so, it will be understood that the methods are not limited to the administration of insulin but also may be applicable to other liquids generally or to administration of other drugs including, but not limited to, pain relievers, cancer drugs, and growth hormones.

BRIEF DESCRIPTION OF THE DRAWINGS

Though the specification concludes with claims particularly pointing out and distinctly claiming the invention, it is believed that the present invention will be better understood from the following description taken in conjunction with the accompanying drawings, in which:

DETAILED DESCRIPTION

In the following detailed description, example administration devices and example methods for setting a dose amount are described in greater detail with reference to the figures. It will be understood that, even when specific embodiments are directed to administration of insulin, the same embodiments are equally applicable to administration of liquids generally and also to administration of other drugs including but not limited to pain relievers, cancer drugs, and growth hormones.

An administration device for administering a liquid drug in adjustable doses may comprise an injection unit with manually operated dose setting components and a dosing mechanism. The manually operated dose setting components may adjust the dosing mechanism to administer an administration dose amount AD of the liquid drug. The administration device may further comprise an electronic indication unit that indicates a relationship, for example, the arithmetic difference, between the administration dose amount AD and a target dose amount TD. In example embodiments, the liquid drug may be insulin and the administration device may be used for the therapy of diabetes mellitus.

In example embodiments, the manually operated dose setting components may comprise a rotatable dose setting knob. For determining the administration dose amount AD, Furthermore, an encoder may be provided for converting the rotation of the dose setting knob to an electrical signal indicative of the administration dose amount AD. In example embodiments, the drug administration may be performed after dose setting by pressing down the dose setting component or dose setting knob.

The indication unit may be operatively coupled to or may comprise further electronics components such as a micro controller, an ASIC, or any additional electronic circuitry known in the art. The indication unit may be configured as part of an electronics module of the injection device. The indication unit may comprise a display. For example, the display may be a liquid crystal display (LCD) adapted to indicate at least numeric values and application specific symbols. Alternatively, the display may be adapted to display alphanumeric values or as a graphical display.

In some embodiments, the display may indicate at least one of the administration dose amount AD, the target dose amount TD and the dose amount deviation $\Delta D$, such that the dose amount deviation $\Delta D$ corresponds to the deviation between the administration dose amount AD and the target dose amount TD. For example, the dose amount deviation $\Delta D$ may be the difference between the administration dose amount AD and the target dose amount TD. In further embodiments, the display indicates all of the administration dose amount AD, the target dose amount TD and the dose amount deviation $\Delta D$.

In some embodiments, the relationship between the administration dose amount AD and the target dose amount TD may be indicated by dedicated symbols on the display. For example, a first symbol may be provided to indicate that the administration dose amount AD does not equal the target dose amount TD, and a second symbol may be provided to indicate that the administration dose amount AD equals the target dose amount TD. In some embodiments, a first arrow symbol and a second arrow symbol are provided, the first arrow symbol indicating that the administration dose amount AD is smaller than the target dose amount TD and the second arrow symbol indication that administration dose amount AD is larger than the target dose amount TD.

In further example embodiments, the display indicates a graphical representation of the dose amount deviation $\Delta D$. For this purpose, the display indicates a graduated dose scale showing also an administration dose mark corresponding to the administration dose amount AD, and a target dose mark corresponding to the target dose amount TD. From the relative positions of the administration dose mark and the target dose mark, the dose amount deviation $\Delta D$ is easily obtained. In this type of embodiment, equivalence of the administration dose amount AD and the target dose amount TD is visible by an alignment of the administration dose mark and the target dose mark on the scale.

In still further example embodiments, the indication unit may comprise other kinds of optical indicators in addition to or instead of the display. The other optical indicators may include, for example, luminous indicators, such as light emitting diodes (LEDs). Luminous indicators may facilitate usage of the administration device under inadequate lighting conditions where a display may be hard to read and also may facilitate usage by the visually impaired.

For example, a single LED may be provided to indicate if the administration dose amount AD equals the target dose or TD or to indicate if the administration dose amount AD does not equal the target dose amount TD. In further embodiments, a multi-color LED is provided, the color of the LED indicating the relation between the administration dose amount AD and the target dose amount TD. For example, a three-colored LED may be red if the deviation between the administration dose amount AD and the target dose amount TD is larger than, e.g., 0.5 IU, yellow if the deviation between administration dose amount AD and target dose amount TD is smaller than 0.5 IU, and green if the administration dose amount AD equals the target dose amount TD. Alternatively or additionally, a multi-color LED may be provided to indicate if the administration dose amount AD is smaller than the target dose amount TD, equals the target dose amount TD or is larger than the target dose amount TD. In further embodiments, a plurality of LEDs are provided, such as, for example, to depict a scale.

In some embodiments, the indication unit may further comprise at least one of an acoustic indicator, such as a buzzer, and a tactile indicator, such as a vibrator. An acoustic indicator or a tactile indicator may be activated, for example, if the administration dose amount AD equals the target dose amount TD or if administration dose amount AD does not equal the target dose amount TD. In example embodiments, the acoustic indicator, the tactile indicator, or both, also may indicate the dose amount deviation $\Delta D$. In further examples, the acoustic indicator, the tactile indicator, or both, may be activated intermittently, such as with the activation pulse frequency dependent on the dose amount deviation $\Delta D$. Alternatively, an acoustic indicator may be activated with a sound frequency or intensity that is dependent on the dose amount deviation $\Delta D$. In further embodiments, the relation between the administration dose amount AD and the target dose amount TD may be indicated via speech output.

In still further example embodiments, the administration device may further comprise a data interface. The data interface may serve several purposes, such as the transmission of configuration data from an external device to the administration device. The administration device may be adapted to store the delivered amounts of administered doses in a history memory together with a time stamp. The time stamp may comprise a date portion and a time-of day portion and be generated, for example, by a clock circuit of the administration device. The history may be downloaded to an external device via the data interface. In specific example embodiments, the data interface is a bidirectional interface and may be a wireless infrared interface or an RF interface such as a BLUETOOTH interface. The external device may be, for example, a Personal Computer (PC), a mobile phone, a Personal Digital Assistant (PDA), or an application specific device.

In some embodiments, a target dose amount TD may be transmitted to the administration device from an external device via the data interface of the administration device. In some embodiments, the target dose amount TD may be stored in the administration device. In the framework of diabetes therapy, for example, storage of the target dose may aid daily administration of long-acting insulin at the same time of day with the same dose amount to cover a diabetic's basal insulin demand. Likewise, storage of the target dose may aid in other therapies, such as pain therapy, where preset dose amounts of an pain-relieving drug are routinely administered.

In some embodiments, several alternative values for the target dose amount TD may be stored in the administration device. Storage of several alternative values may be useful, for example, if a long-acting insulin is to be administered in different doses at different times of day. For each administration, the target dose amount TD may be manually or automatically selected by the administration device depending on the time of day. A target dose to be stored in the administration device may be factory set or may be transferred to the administration device, for example, from an external device.

In further embodiments, the administration device may comprise one or more data entry component. The data entry component may be adapted for the entry of therapy related data. The data entry component may be realized, for example, by one or several push-buttons. Alternatively from or in addition to push-buttons, the data entry component may comprise more highly sophisticated input means, such as a joystick. In some embodiments, the data entry component may comprise a crossbar switch. In further embodiments, therapy related data entered via the data entry component may be stored in a history memory together with a time stamp indicating the time of entry. In still further embodiments, the history may be downloaded via the data interface of the administration device to an external device. For example, therapy related data entered via the data entry component may be downloaded together with the dose history. In the framework of diabetes therapy, for example, the therapy-related data may comprise at least one or both of a carbohydrate amount or a blood glucose value.

In some embodiments, the administration device may further comprise a dose calculator for calculating a calculated dosage $D_{calc}$ based on therapy related data, wherein the target dose amount TD is set to the calculated dosage $D_{calc}$. In the framework of diabetes therapy, for example, the therapy related data may comprise the carbohydrate amount of food to be consumed by the patient. The calculated dosage $D_{calc}$ for covering an intake of food may be calculated based on a first set of factors taking into consideration patient-specific needs or the time of day so as to specify the amount of insulin to cover a given carbohydrate intake. The first set of factors may be uploaded to the administration device as configuration data from an external device via a data interface but also may be manually entered via the data entry component of the administration device. Similarly, an appropriate calculated dosage $D_{calc}$ for correcting an undesirably elevated blood glucose value may be calculated by the dose calculator based on a second set of factors that are patient-specific or dependent on the time-of-day so as to specify the amount of insulin required to correct an undesired elevation of blood glucose level.

In further embodiments, the therapy related data may additionally comprise adjustment factors related to one or more of a level or duration of strenuous activity, a level of mental stress, data related to illnesses, or data related to the intake or administration of additional drugs. In the framework of pain therapy, a calculated dosage $D_{calc}$ may be calculated based, at least in part, on a current pain level.

Therapy related data on which the calculation of the calculated dosage $D_{calc}$ is based may be entered via the data entry component. Alternatively or in addition, the therapy related data may be transmitted to the administration device from an external device via a data interface connected to the administration device. In some embodiments, the administration device may comprise a blood glucose meter to provide blood glucose values. In addition to or as an alternative to the administration device's comprising a blood glucose meter, blood glucose values may be transmitted to the administration device from an external blood glucose meter such as a commercially available strip-based blood glucose meter, for example, ACCU-CHEK® Compact plus or ACCU-CHEK® Aviva.

In example embodiments entailing use of the administration device in the framework of diabetes therapy, the administration device may comprise a carbohydrate amount database. The carbohydrate amount database may store, for example, relative or absolute carbohydrate amounts of a number of meals, such that a meal may be selected from the carbohydrate amount database via the data entry component.

Thereby, the carbohydrate amount database may facilitate simple and user-friendly entry of carbohydrate amounts without a further need for the user to calculate or estimate the carbohydrate amount.

For example, for meals having a well defined and fixed carbohydrate amount, such as many fast-food meals, the absolute carbohydrate amount may be stored in the carbohydrate amount database. For meals of variable size, a relative carbohydrate amount may be stored in the database, and additional information specifying the meal size may be entered by the patient via the data entry component. The meal size may be either quantitative or semi-quantitative, such as "large," "medium," or "small," for example. In some embodiments, the administration device may be configured such that all or a part of the administration device may be held in the operator's hand during a drug administration.

In some embodiments, all components of the administration device may be enclosed within an elongated housing, such as a pen-shaped housing. Alternatively, the components of the administration device may be enclosed by a plurality of housings adapted to be physically connected so as to have an overall elongated shape, such as a pen-like shape.

Figure 1:
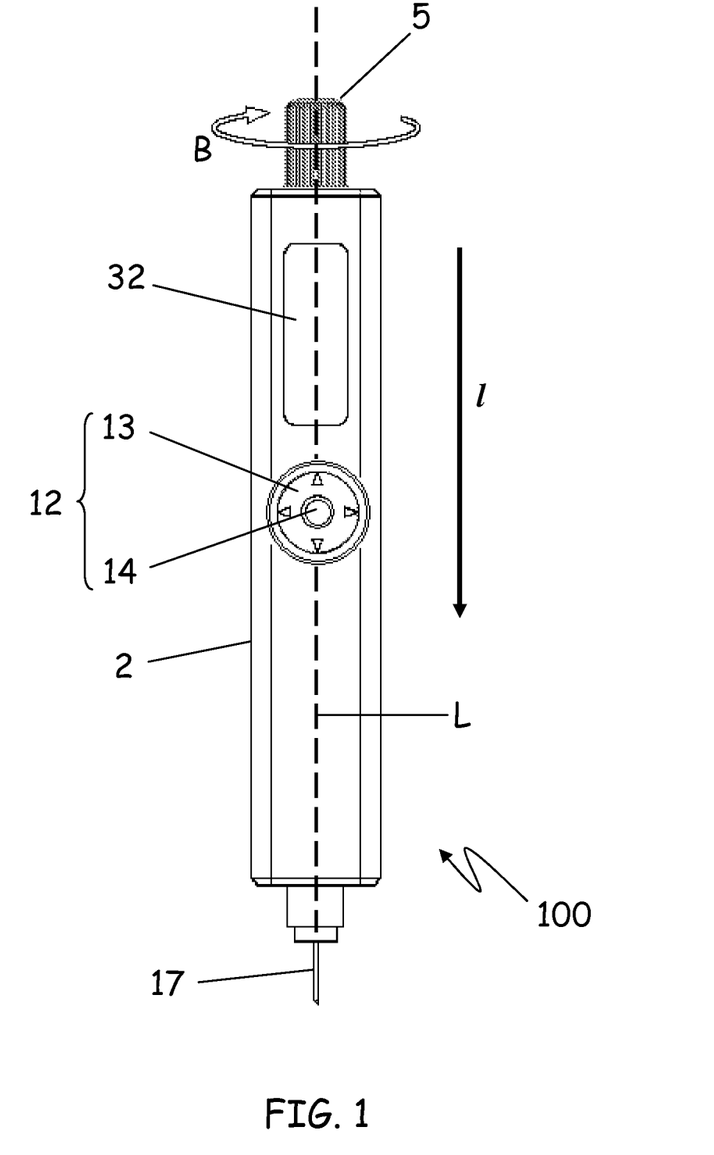
FIG. 1 shows a first example embodiment of an administration device adapted to carry out one or more example methods described herein for setting a dose amount.

FIG. 1 shows a first example of an administration device 100 for the self-administration of a liquid such as, for example, insulin Most components of the administration device 100 are enclosed by a housing 2, depicted in FIG. 1 as pen-shaped. The housing 2 comprises coupling means (not shown) for releasable coupling with an injection cannula 17, the injection cannula 17 projecting from the housing 2 into the direction indicated by vector 1, vector 1 being parallel to longitudinal axis L of housing 2.

The injection cannula 17 may be disposable to facilitate use for a single injection for sterility reasons. In other embodiments, the injection cannula 17 may be used for multiple injections. A cover (not shown in FIG. 1) may be provided to cover the cannula coupling means or the injection cannula 17, respectively.

A dose setting knob 5 may serve as the dose setting component for setting an insulin administration dose amount AD. Dose setting knob 5 is normally in a retracted position inside housing 2 and may be extended by pressing a release key (on the backside of housing 2, not visible). In its extended position, dose setting knob 5 may be rotated clockwise through rotational direction B to increase the administration dose amount AD or may be rotated counterclockwise (against rotational direction B) to decrease the administration dose amount AD. The minimum dose amount increment may be defined by rotational catching positions corresponding to, e.g., 0.5 IU (International Units), with a full rotation of dose setting knob 5 corresponding to, e.g., 20 IU. After setting the administration dose amount AD, the patient may grip the device with one hand and perform the injection by (i) piercing the skin of, e.g., an upper arm or thigh, by moving the device into direction 1 toward the skin, and (ii) driving a dosing mechanism 6 to administer the insulin dose by slowly pressing the dose setting knob 5 down and back into its retracted position. Alternatively, the manually driven dosing mechanism may be designed according to the disclosure of WO 93/16740 or another suited design known in the art.

Figure 2:
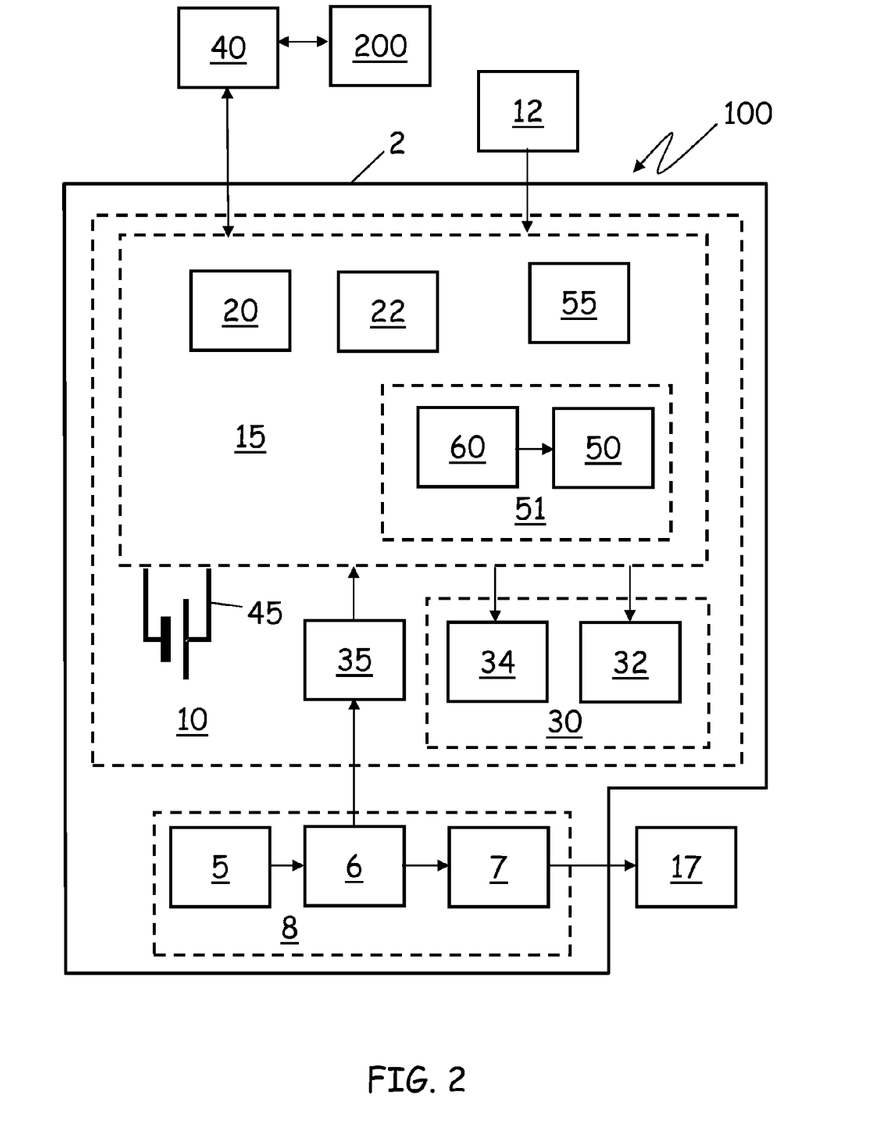
FIG. 2 shows a schematic functional diagram representing embodiments of the device shown in FIG. 1.

Referring to both FIG. 1 and the schematic structural diagram of FIG. 2, further components and connections are described through example embodiments of an administration device 100. In the administration device 100, dose setting knob 5 acts on dosing mechanism 6. When dose setting knob 5 is pressed down into its retracted position, dosing mechanism 6 forces a plunger of insulin cartridge 7 forward in the direction indicated by vector 1, resulting in an insulin dose being administered via the injection cannula 17. In combination, the dose setting knob 5, the dosing mechanism 6, and the insulin cartridge 7 form the injection unit 8.

For scanning the rotational movement of dose setting knob 5, encoder 35 may be provided to detect the rotation of dose setting knob 5 and transfer a corresponding electrical signal to controller 15 dependent on the direction of the rotation. In example embodiments not shown, the encoder 35 may comprise a set of linear cam followers driven by a crank shaft, a set of cam discs, or any similar arrangement comprising cam followers operatively coupled to a corresponding set of electrical contacts. Similarly, optical encoders or magnetic encoders with magnets and Hall sensors may be employed. In further example embodiments, the encoder may be configured according to any of the types of encoders disclosed in WO 93/16743.

The administration device 100 may include an electronics module 10 fulfilling multiple functions. The core element of the electronics module 10 is controller 15 realized, for example, as an Application Specific Integrated Circuit (ASIC). Most of the further elements of the electronics module 10 are integral with controller 15. Controller 15 is operatively coupled with an indication unit 30. A display 32, such as, for example, a liquid-crystal display (LCD), is provided for showing numeric data and application specific data. When the dose setting knob 5 is rotated, the dose amount is computed by controller 15 based on the signals generated by encoder 35 and is displayed on display 32. Besides display 32, indication unit 30 may comprise a buzzer 34 for acoustic notification and indication purposes. Display 32 and, optionally, buzzer 34 may be configured to indicate if the administration dose amount AD equals the target dose amount TD and to indicate dose amount deviation ΔD. When a liquid such as, for example, insulin is administered, the dose amount is stored in memory 20 together with a time stamp generated by clock circuit 22, the time stamp comprising a time of day portion and a date portion.

One or more data entry components 12 may be especially suited for entering carbohydrate amount data but also may be used for further data entry and control operations. In the example embodiment shown in FIG. 1, the data entry components 12 are configured as a crossbar switch 13 with an ENTER key 14 in the center of the crossbar switch 13. This arrangement allows for an ergonomic one-handed operation.

The electronics module 10 may further comprise a power supply 45, shown, for example, as a replaceable or non-replaceable battery 45. The electronics module 10 may be configured to change from standby to regular operation whenever dose setting knob 5 is extended or when data entry components 12 are operated. The electronics module 10 may change from regular operation to the standby state occur if no operation is being performed for a threshold time of, e.g., 2 minutes.

In some embodiments, carbohydrate amounts may be entered in carbohydrate exchange units used by many diabetics. However, other units may be used such as, for example, grams of carbohydrates. The controller 15 may be configured by the patient or by the healthcare professional for carbohydrate amount entry in the desired units.

In specific example embodiments, the electronics module 10 may operate such that, after a carbohydrate amount is entered, the entry is confirmed and completed when the user presses the ENTER key 14, to cause the carbohydrate amount to be stored in memory 20 together with a time stamp generated by clock circuit 22. If the user does not modify the entered amount of carbohydrates or does not press the ENTER key 14 within a certain time of, e.g. 5 sec, the entry is canceled.

In specific example embodiments pertaining to administration of insulin. an appropriate dosage amount required to compensate for food intake is directly correlated with the carbohydrate amount. As such, the required calculated dose amount $D_{calc}$ may be automatically calculated based on the carbohydrate amount entered via data entry components 12. For this purpose, dose calculator 55, integral with controller 15, may be loaded with an appropriate algorithm. The calculated dose amount $D_{calc}$ is calculated based on a first set of patient-specific and time-of-day dependent proportionality factors. The first set of proportionality factors may be uploaded to the electronics module 10 from a data interface 40 or may be entered via data entry components 12. The calculated dose amount $D_{calc}$ may be stored in memory 20 along with the carbohydrate amount entered via data entry components 12.

After the calculated dose amount $D_{calc}$ is calculated, it is displayed on display 32. The calculated dose amount $D_{calc}$ may either be directly accepted for administration or may be modified via data entry components 12. This may be necessary, e.g., to compensate for strenuous activity or an undesirably high or low blood glucose value. Afterwards, an administration dose amount AD may be manually set and administered using dose setting knob 5 as described above. Though an administration dose amount AD different from the calculated dose amount $D_{calc}$ may be administered intentionally in certain exceptional situations, it is normally important to ensure that the administration dose amount AD equals the calculated dose amount $D_{calc}$ For this purpose, a dose comparator 51 is provided. The dose comparator 51 may comprise a difference calculator 60 and a zero detector 50. The calculated dose amount $D_{calc}$ may be fed into difference calculator 60 as the target dose amount TD, and difference calculator 60 may calculate the dose amount deviation ΔD between the administration dose amount AD and the target dose amount TD. The dose amount deviation ΔD is fed into zero detector 50. Zero detector 50 indicates if dose amount deviation ΔD is zero, indicating that the administration dose amount AD equals target dose amount TD.

Figure 3A:
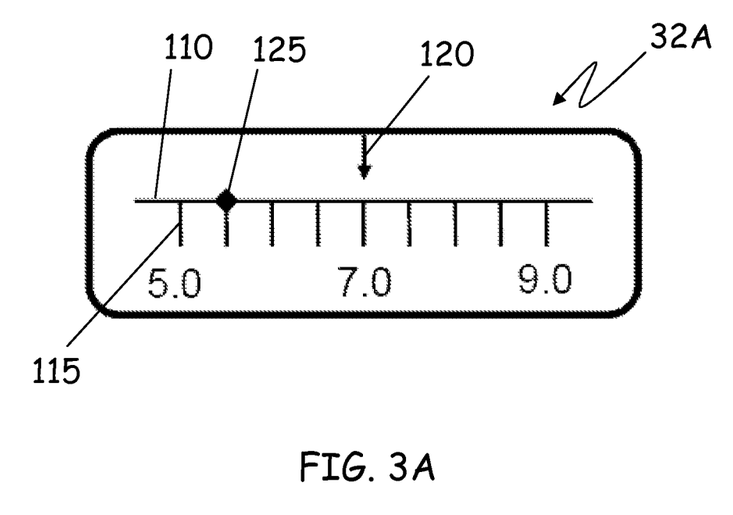
FIG. 3A and FIG. 3B show an example outputs of a display belonging to an indication unit of the administration device shown in FIG. 1 and represented in FIG. 2.
Figure 3B:
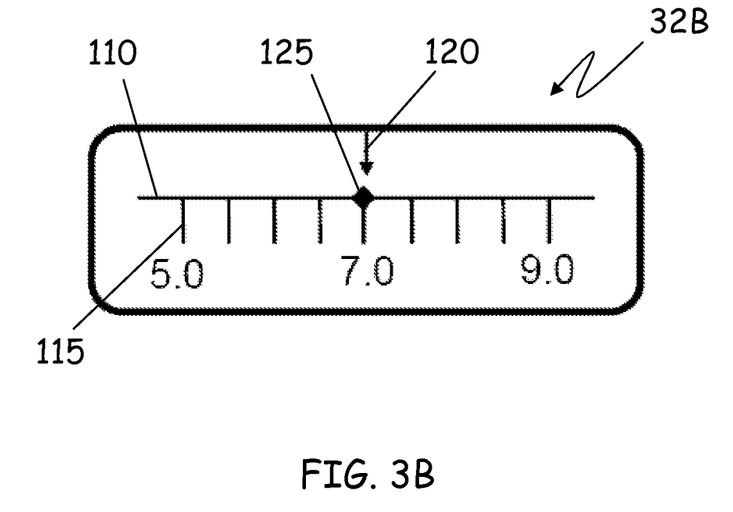

FIG. 3A and FIG. 3B show example outputs of display 32A and display 32B, respectively, for a dose amount of $D_{calc}$=7.0 IU of insulin. The dose of 7.0 IU of insulin may have been calculated by dose calculator 55 to cover a carbohydrate amount entered via data entry components 12 to effect entry of a target dose amount of TD=$D_{calc}$=7.0 IU into difference calculator 60 of dose comparator 51, as described above and illustrated schematically in FIG. 2.

In the example embodiment depicted in FIG. 3A, the display 32A shows a dose scale 110 with graduations 115. The dose scale 110 is calculated and arranged such that the target dose amount TD is located at the center of the dose scale 110. The range of the dose scale 110 is from TD−2.0 IU to TD+2.0 IU. The target dose amount TD is further indicated by a target dose mark 120, shown as an arrow, for example. An administration dose mark 125, shown as a diamond, for example, indicates the administration dose amount AD. Rotation of the dose setting knob 5 causes the administration dose mark 125 to move on the dose scale 110. FIG. 3A shows the display 32A for administration dose amount AD=5.5 IU, and FIG. 3B shows the display 32B for ΔD=TD=7.0 IU. In the display 32B, target dose mark 120 and administration dose mark 125 are aligned. The alignment of administration dose mark 125 and target dose mark 120 would generally be sufficient to indicate the equivalence of administration dose amount AD and target dose amount TD. However, zero detector 50 may additionally be used to supply a further and more explicit indication. For example, target dose mark 120 may blink when administration dose amount AD does not equal target dose amount TD and be shown continuously if administration dose amount AD equals target dose amount TD. Alternatively or additionally, an acoustic indication may be provided via buzzer 34.

If administration dose amount AD is not in the range of the dose scale 110, the numeric value of administration dose amount AD may be shown on display 32 instead of on the dose scale 110. The numeric value of the target dose amount TD may be displayed additionally. If administration dose amount AD is administered to a patient without administration dose amount AD being equal to target dose amount TD, an appropriate warning may be shown on display 32 or an acoustic warning may be provided via buzzer 34.

In further example embodiments, comparison of administration dose amount AD with target dose amount TD and control of the display 32 to indicate when administration dose amount AD equals target dose amount TD may be performed continuously during the setting of the administration dose amount AD. For example, when the dose setting knob 5 is rotated, the difference between administration dose amount AD and target dose amount TD may be displayed in real-time and the equivalence of administration dose amount AD and target dose amount TD may be indicated in real-time.

In example embodiments, data stored in memory 20 may be downloaded to an external device 200 by means of data interface 40, for example. As specific examples, data interface 40 may comprise one or more interfaces selected from a wireless infrared interface or an RF interface such as a BLUETOOTH interface. For downloading purposes, a DOWNLOAD HISTORY function may be provided, which may be selected via data entry components 12. The external device 200 may be any device such as a PC, a PDA, or a cell phone, for example.

In further example embodiments, data interface 40 may be used not only for history download, but to upload data from the external device 200 to the administration device 100. For example, the data interface 40 may be used to set configuration data such as time and date in the clock circuit 22, or the preferred unit for entering carbohydrate amounts and proportionality factors with the dose calculator 55. Furthermore, the data interface 40 may be used to upload a target dose amount TD from the external device 200 into memory 20. This kind of target dose amount TD may be a dose required for covering the basal insulin need, for example, with an insulin dose of the same amount being administered every day and at the same time of day. The target dose amount TD may be uploaded to the administration device by a healthcare professional, for example.

In alternative embodiments, the administration device may be configured as a dual-module administration device comprising an injection module and a supplementary module. In this type of embodiment, the injection module comprises the injection unit and the indication unit. The injection module further comprises an injection module data interface and an injection module housing. The supplementary module comprises a supplementary module data interface and a supplementary module housing. The supplementary module data interface is adapted to transmit a value corresponding to the target dose amount TD to the injection module data interface.

In example embodiments, the supplementary module further comprises a data entry component for entering therapy related data, which may be realized as touch screen, for example. Because only a limited number of elements is required on the injection module according to this type of embodiment, the injection module may be especially slim, lightweight, and cheap. In addition, the indication unit may be rather simple and comprise, e.g., a substantially numeric LCD display in combination with a more sophisticated user interface in the supplementary module.

In further alternative embodiments, the administration device also comprises an injection module and a supplementary module. The injection module comprises the injection unit and further comprises an injection module data interface and an injection module housing. The supplementary module comprises the indication unit and further comprises a supplementary module data interface and a supplementary module housing. The injection module data interface may be adapted to transmit to the supplementary module device data interface a value corresponding to the administration dose amount AD. Because the injection module only comprises a minimum number of components, the injection module may be rather slim, lightweight, and inexpensive.

In all embodiments comprising an injection module and a supplementary module, the injection module may be adapted to be held in the operator's hand during administration of a drug administration and may be pen-shaped. In all embodiments comprising an injection module and a supplementary module, the supplementary module may have the form of a Personal Digital Assistant (PDA) or a mobile phone. In specific example embodiments, the supplementary module may be a commercially available device such as a PDA or a cell phone.

In further embodiments comprising an injection module and a supplementary module, the injection module, the injection module data interface, and the supplementary module data interface may form a bidirectional communication interface. In specific example embodiments the bidirectional communication interface may comprise a wireless infrared interface, a BLUETOOTH RF interface, a wired interface, such as a Universal Serial Bus (USB) interface, or any combination of these.

Figure 4:
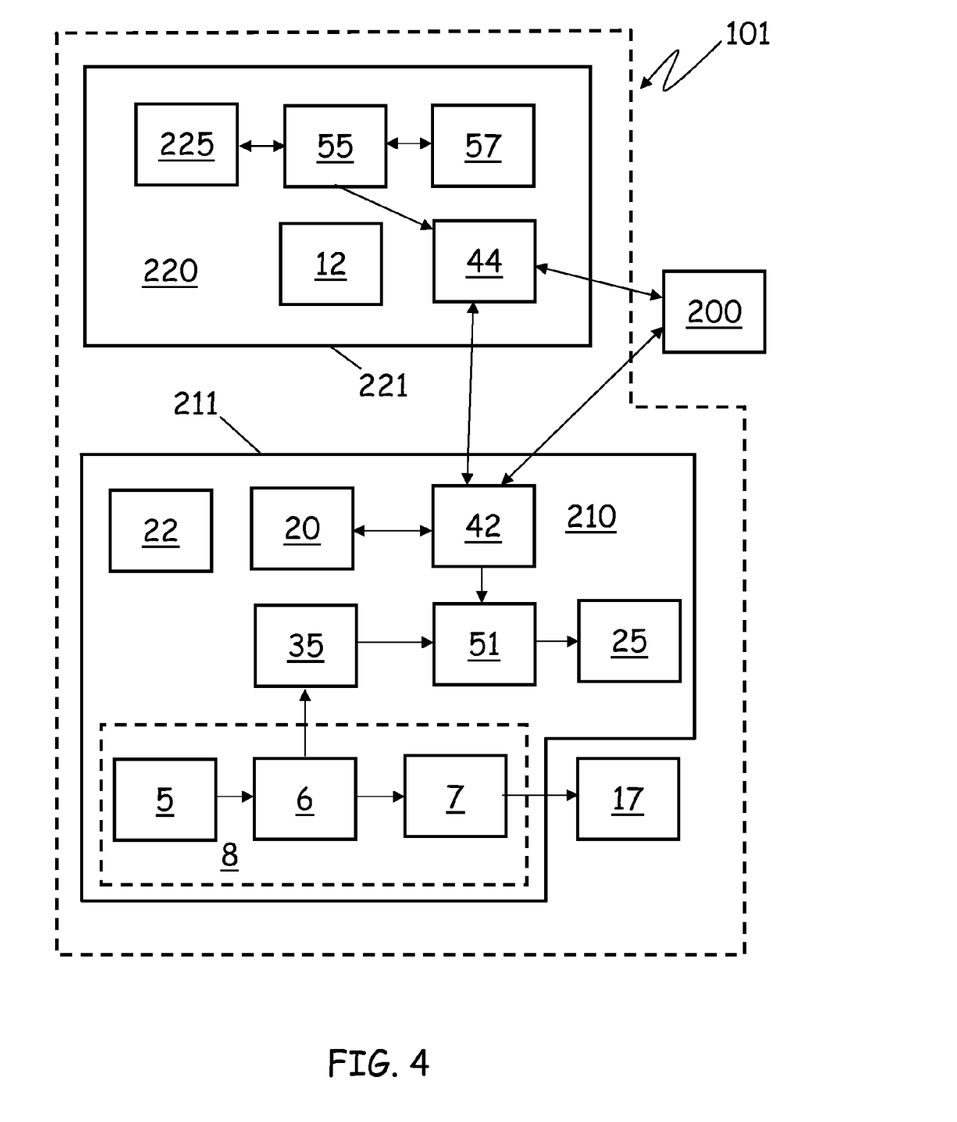
FIG. 4 shows a schematic functional diagram of an example embodiment administration device configured as a dual-module administration device and being adapted to carry out one or more example methods described herein for setting a dose amount.

FIG. 4 shows a structural diagram of an example embodiment of an administration device configured as a dual-module administration device 101. The dual-module administration device 101 comprises an injection module 210 and a supplementary module 220.

An injection unit 8, an injection module data interface 42, a dose comparator 51 and an injection module indication unit 25 belong to the injection module 210 and are enclosed by an injection module housing 211. Injection module housing 211 may have a substantially pen-shaped form, for example, similar to the form of the administration device 100 shown in FIG. 1. Data entry components 12, dose calculator 55, and a supplementary module data interface 44 belong to the supplementary module 220 and are enclosed within a supplementary module housing 221. In non-limiting example embodiments, the supplementary module housing 221 may be slim and substantially box-like, similar to a PDA. Though not explicitly shown in FIG. 4, supplementary module 220 may comprise further components such as a power supply, a memory, a clock circuit, data output means, for example.

After a carbohydrate amount is entered by a user, for example via data entry components 12, the corresponding calculated dose amount $D_{calc}$ may be calculated by dose calculator 55 and transmitted from supplementary module data interface 44 to injection module data interface 42. A dose may be subsequently set via dose setting knob 5 as described above with respect to the administration device 100 depicted in FIGS. 1 and 2.

In some embodiments, the injection module indication unit 25 referenced in FIG. 4 may comprise a display (not shown) identical to the display 32 shown FIGS. 1 and 2 and described above. Alternatively, the injection module indication unit 25 may comprise a simpler display (not shown) such as, for example, a purely numerical display with additional symbols to indicate if administration dose amount AD equals target dose amount TD. A simpler display in the injection module indication unit 25 of the dual-module administration device 101 may be especially suitable, particularly when the injection module indication unit 25 is not intended to be used to show further data such as therapy related data. Alternatively, the injection module indication unit 25 may comprise a mechanical display (not shown) operatively coupled to dose setting knob 5, and the mechanical display may be used to display administration dose amount AD. Also alternatively, the injection module indication unit 25 may comprise other types of optical indicators (not shown), such as optical indicators comprising, e.g., one or more LED. Likewise, the injection module indication unit 25 may comprise a buzzer (not shown) to indicate to the user when administration dose amount AD equals target dose amount TD.

The dual-module administration device 101 may comprise data entry components 12 as a component of the supplementary module 220. Such a configuration allows the injection module housing 211 to be especially slim and lightweight, if desired. Furthermore, it allows additional freedoms to design the data entry components 12 for greater user comfort and user-friendly operation. In specific example embodiments, the data entry components 12 of the dual-module administration device 101 may be incorporated, for example, as a touchscreen, a crossbar switch, a data-entry wheel, a keyboard, a similar device known in the art, or any combination of such elements.

Supplementary module 220 may further include a carbohydrate amount database 57. Carbohydrate amount database 57 stores the relative or absolute carbohydrate amounts of a number of meals and is operatively coupled to dose calculator 55. Typical or frequently taken meals may be comfortably selected from carbohydrate amount database 57 without requiring the repeated direct entry of carbohydrate amounts.

Supplementary module 220 may further comprise a glucose meter 225 for the self-determination of blood glucose values. The glucose meter 225 may employ disposable, single-use test strips known in the art. Glucose meter 225 is operatively coupled to dose calculator 55. To calculate a calculated dose amount $D_{calc}$ for an insulin dose required to compensate for undesirably high blood glucose values, a second set of patient-dependent and time-of-day dependent proportionality factors specifying the dose amount of an insulin dose required to correct a given raise in blood glucose is provided. Based on this second set of proportionality factors, the dose calculator 55 automatically calculates the appropriate insulin dose amount $D_{calc}$. This dose is afterwards transmitted from supplementary module data interface 44 to injection module data interface 42.

As for insulin doses for covering carbohydrate intake, calculated dose amount $D_{calc}$ is fed as target dose amount TD into dose comparator 51, and administration dose amount AD is set via dose setting knob 5. Because blood glucose measurements and the administration of insulin for the compensation of undesirably high blood glucose values are often performed directly prior to a meal, a combined calculated dose amount $D_{calc}$ may be calculated, taking into account both the insulin required to compensate for an undesired high blood glucose value and the carbohydrate intake. If the blood glucose value is undesirably low, the combined calculated dose $D_{calc}$ may also be smaller than the dose amounts that would be calculated without considering the blood glucose value.

Alternatively from or in addition to receiving blood glucose measurements from glucose meter 225, supplementary module 220 may receive blood glucose data from an external blood glucose meter (not shown) via supplementary module data interface 44 or from an additional data interface (not shown). In further example embodiments, blood glucose values may be determined using a blood glucose meter and then the values may be entered manually using data entry components 12.

In a specific example embodiment, the injection module data interface 42 and the supplementary module data interface 44 may communicate bidirectionally according to a common standard, such as via infrared. Data stored in memory 20 may be directly downloaded to an external device 200 via injection module data interface 42. Alternatively, data stored in memory 20 may be first transmitted to supplementary module 220 via injection module data interface 42 and supplementary module data interface 44. Thereupon, the data may be transmitted from supplementary module 220 to external device 200 via supplementary module data interface 44. Supplementary module data interface 44 may comprise multiple interface means. In a particular embodiment, the supplementary module data interface 44 may communicate with the injection module data interface 42 via infrared and communicate with external device 200 via more powerful means such as BLUETOOTH or a wired Universal Serial Bus (USB).

Though the administration device 100 in FIG. 2 and the dual-module administration device 101 in FIG. 4 have been described separately, in still further example embodiments various elements of the administration device 100 and the dual-module administration device 101 may be combined or interchanged. As a specific example, an administration device 100 may be used as a stand-alone device in situations where it is undesirable to carry an supplementary module 220. Even so, the user sometimes may prefer to use a supplementary module 220 with the administration device 100 to gain advantages such as a more comfortable configuration of the data entry components 12 and ready access to information in the carbohydrate amount database 57, without necessarily relying at all times on the particular configuration of the dual-module administration device 101 described above.

Further example embodiments are directed to methods for setting a dose amount of a liquid drug for administration. In the example methods, unintended deviation of an administration dose amount AD from a target dose amount TD may be prevented.

In one example embodiment, a method for setting a dose amount may comprise providing an administration device according to one or more embodiments described herein. For example, the administration device may comprise an injection unit and an indication unit. The injection unit may have a dosing mechanism and a manually operated dose setting component configured to adjust the dosing mechanism to administer an administration dose amount of the liquid drug. The indication unit may be configured to indicate a relationship between the administration dose amount and a target dose amount stored in or entered into the administration device. The method may further comprise operating the manually operated dose setting component to adjust the dosing mechanism to correspond to an administration dose amount relative to the target dose amount. The method may further comprise continuing to operate the manually operated dose setting component until the indication unit indicates that the administration dose amount is equal to the target dose amount.

In example embodiments, the administration device may further comprise a memory, and the target dose amount may be stored in the memory. In further example embodiments, the administration device may further comprise one or more data entry component, and the method may further comprise manipulating the one or more data entry component to enter the target dose amount into the administration device.

With regard to the indication unit, the relation between the administration dose amount and the target dose amount may be determined by electronic circuitry within the indication unit or by further electronics components such as a micro controller, an ASIC, or other electronic circuitry known in the art.

In still further example embodiments, the indication unit may comprise at least one indicator selected from the group consisting of an optical indicator, an acoustic indicator, and a tactile indicator.

In some cases, it may be desirable for the administration dose amount AD to deviate from the target dose amount TD, in which case a deviation may be made intentionally during the operation of the manually operated dose setting mechanism. In the framework of insulin administration for the therapy of diabetes mellitus, this may be the case, e.g., when taking in carbohydrates immediately before, during, or after strenuous activities that generally result in a reduced insulin demand. In most cases, however, administering of an administration dose amount AD different from the target dose amount TD happens only by mistake. Therefore, the administration device provided in the method for setting a dose amount may comprise a warning indicator to provide a warning after the administration dose amount AD is administered when the administration dose amount AD did not the equal the target dose amount TD. The warning indicator may comprise at least one indicator selected from the group consisting of an optical indicator, an acoustic indicator, and a tactile indicator.

In specific example embodiments, the methods for setting a dose amount of a liquid drug may be applied for the administration of insulin in the framework of diabetes mellitus therapy. Even so, it will be understood that the methods are not limited to the administration of insulin but also may be applicable to other liquids generally or to administration of other drugs including, but not limited to, pain relievers, cancer drugs, and growth hormones.

What is claimed is:

1. An administration device for administering a liquid drug in adjustable doses, the administration device comprising:
   an injection unit having a dosing mechanism and a manually operated dose setting component that sets an administration dose amount of the liquid drug to be administered by the dosing mechanism; and
   an electronic indication unit comprising a display that graphically indicates before administration of the liquid drug a dose amount deviation equal to the difference of the administration dose amount set using the dose setting component and a target dose amount stored in or entered into the administration device.

2. The administration device of claim 1, wherein the electronic indication unit further comprises a warning indicator that warns after administration of the liquid drug that the administration dose amount did not equal the target dose amount, the warning indicator being selected from the group consisting of an optical indicator, an acoustic indicator, a tactile indicator, and combinations thereof.

3. The administration device of claim 1, further comprising a data interface.

4. The administration device of claim 3, wherein the data interface transmits the target dose amount to the administration device from an external device.

5. The administration device of claim 1, wherein the administration device is configured to be handheld during administration of the liquid drug.

6. The administration device of claim 1, further comprising:
an injection module comprising the injection unit, the electronic indication unit, an injection module data interface, and an injection module housing; and
a supplementary module comprising a supplementary module data interface and a supplementary module housing,
wherein the supplementary module data interface transmits the target dose amount to the injection module data interface.

7. The administration device of claim 1, further comprising:
an injection module comprising the injection unit, an injection module data interface, and an injection module housing; and
a supplementary module comprising the electronic indication unit, a supplementary module data interface, and a supplementary module housing,
wherein the injection module data interface transmits an administration dose amount to the supplementary module data interface.

8. The administration device of claim 1, wherein the target dose amount is stored in a memory disposed in the administration device.

9. The administration device of claim 1, further comprising one or more data entry component.

10. The administration device of claim 9, further comprising a dose calculator for calculating a calculated dose amount $D_{calc}$ based on therapy related data.

11. The administration device of claim 10, wherein the therapy related data comprise a carbohydrate amount, a blood glucose value, or both.

12. The administration device of claim 10, further comprising a carbohydrate amount database operatively coupled to the dose calculator.

13. The administration device of claim 1, further comprising a blood glucose meter.

14. The administration device of claim 1, wherein the display indicates before administration of the liquid drug a graduated dose scale showing an administration dose mark corresponding to the administration dose amount and a target dose mark corresponding to the target dose amount, whereby the dose amount deviation is graphically indicated from the relative positions of the administration dose mark and the target dose mark.

15. The administration device of claim 14, wherein the graduated dose scale has a range from the target dose amount plus 2.0 IU to the target dose amount minus 2.0 IU and the target dose mark is located in the middle of the graduated dose scale.

16. The administration device of claim 1, wherein:
the injection unit comprises a housing and a release key on the housing;
the dose setting component is a dose setting knob having a retracted position inside the housing and an extended position extended outside the housing, the dose setting knob being normally in the retracted position until the release key is pressed.

17. The administration device of claim 16, wherein the dose setting knob is rotatable only in the extended position and rotation of the dose setting knob sets the administration dose amount.

18. The administration device of claim 16, further comprising an electronics module that supplies power to the electronic indication unit, the electronics module being configured to change from a standby mode to a regular operation mode when the dose setting knob is placed into the extended position.

19. A method for setting a dose of a liquid drug for administration to a patient, the method comprising:
providing an administration device, the administration device comprising an injection unit and an electronic indication unit, the injection unit having a dosing mechanism and a manually operated dose setting component that sets an administration dose amount of the liquid drug to be administered by the dosing mechanism, the electronic indication unit comprising a display that graphically indicates before administration of the liquid drug a dose amount deviation equal to the difference of the administration dose amount set using the dose setting component and a target dose amount stored in or entered into the administration device;
operating the manually operated dose setting component to set the administration dose amount relative to the target dose amount; and
determining the relationship of the administration dose amount relative to the target dose amount from the electronic indication unit.

20. The method of claim 19, wherein the administration device further comprises a memory and the target dose amount is stored in the memory.

21. The method of claim 19, wherein the administration device further comprises one or more data entry component, the method further comprising manipulating the one or more data entry component to enter the target dose amount into the administration device.

* * * * *

UNITED STATES PATENT AND TRADEMARK OFFICE
CERTIFICATE OF CORRECTION

| | |
|---|---|
| PATENT NO. | : 8,870,830 B2 |
| APPLICATION NO. | : 12/778634 |
| DATED | : October 28, 2014 |
| INVENTOR(S) | : Axel Remde |

Page 1 of 1

It is certified that error appears in the above-identified patent and that said Letters Patent is hereby corrected as shown below:

In The Specification

Col. 9, Line 63,
"shows the display 32B for $\Delta D = TD = 7.0$ IU. In the display" should read
--shows the display 32B for $AD = TD = 7.0$ IU. In the display--;

Col. 13, Line 39,
"it is undesirable to carry an supplementary module 220. Even" should read
--it is undesirable to carry a supplementary module 220. Even--; and Col. 14, Line 35,
"when the administration dose amount $AD$ did not the equal" should read
--when the administration dose amount $AD$ did not equal--.

Signed and Sealed this
Fifth Day of January, 2016

Michelle K. Lee
*Director of the United States Patent and Trademark Office*